(12) United States Patent
Kronich et al.

(10) Patent No.: US 7,214,068 B2
(45) Date of Patent: May 8, 2007

(54) LASER RIBBON BOND PAD ARRAY CONNECTOR

(75) Inventors: Christine G. Kronich, St. Paul, MN (US); Todd H. Schaefer, Blaine, MN (US); Scott J. Robinson, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 124 days.

(21) Appl. No.: 11/004,175

(22) Filed: Dec. 3, 2004

(65) Prior Publication Data
US 2006/0122658 A1   Jun. 8, 2006

(51) Int. Cl.
*H01R 12/00* (2006.01)
*H01R 4/02* (2006.01)
*H05K 1/00* (2006.01)

(52) U.S. Cl. .................. 439/65; 439/83; 439/876; 439/909; 607/36; 607/37

(58) Field of Classification Search ............... 607/36, 607/37; 439/65, 909, 83, 876
See application file for complete search history.

(56) References Cited

U.S. PATENT DOCUMENTS

| | | | | |
|---|---|---|---|---|
| 3,867,950 | A * | 2/1975 | Fischell | 607/33 |
| 6,459,935 | B1 * | 10/2002 | Piersma | 607/37 |
| 6,721,602 | B2 * | 4/2004 | Engmark et al. | 607/36 |
| 6,963,780 | B2 * | 11/2005 | Ruben et al. | 607/36 |

* cited by examiner

*Primary Examiner*—Robert E. Pezzuto
*Assistant Examiner*—Natasha Patel
(74) *Attorney, Agent, or Firm*—Daniel G. Chapik; Girma Wolde-Michael

(57) ABSTRACT

A laser ribbon bond pad array connector is disclosed for electrically connecting a RF module to an IMD circuit board in an implantable medical device. The array connector includes a connector body with a plurality of electrically isolated bonding fingers embedded in the connector body. Each bonding finger includes a solder pad that is on a first surface of the connector body and a laser ribbon bond pad that is on a second surface of the connector body. The first and second surfaces are spaced apart in angular relations thereof.

24 Claims, 7 Drawing Sheets

LASER RIBBON BOND PAD ARRAY CONNECTOR

TECHNICAL FIELD

This invention relates generally to implantable medical devices (IMDs) having radio frequency (RF) telemetry capabilities for uplink, transmitting patient data, further IMD and downlink, receiving programming and interrogation commands to and from an external programmer or other medical device, and more particularly, a laser ribbon bond pad array connector used for electrical connection between a RF module and an IMD circuit board within an IMD housing.

BACKGROUND

A wide variety of implantable medical devices (IMDs) that employ electronic circuitry for providing electrical stimulation of body tissue and/or monitoring a physiologic condition are known in the art. IMDs may include implantable pulse generators (IPG), cardiac pacemakers, pacemaker-cardioverter-defibrillators, nerve, muscle and neurological stimulators, cardiomyostimulators, implantable drug dispensers, implantable cardiac signal monitors and recorders, and the like. IMDs typically include a housing that encloses a variety of internal components and isolates them from the implanted environment. IMDs may include integrated circuits, charging capacitors, batteries, and other components that are enclosed in hermetically sealed metallic housings. Within the human body, for example, the housing must be sealed to prevent ingress of fluids that can cause the device to short circuit or corrode internal components, which renders the IMD inoperable.

The IMDs typically comprise a hermetically sealed housing containing the battery and electronic circuitry. Many IMDs are capable of two-way communication or telemetry between the IMD and an external device, (e.g., a programmer). For example, in a pacemaker system, a programmer downloads data to an implanted pacemaker such as operating instructions and software. Likewise, data may flow in the opposite direction; that is, from the implanted pacemaker to the programmer for analysis. In fact, modern pacemakers are capable of storing significant amounts of data about the patient (e.g., average heart rate) and the pacemaker itself (e.g., battery status), which may need to be frequently transmitted to the programmer for evaluation by the physician.

One way of communicating with an IMD is through RF telemetry transmission, which relies upon magnetic field coupling through the patient's skin of an IMD antenna with a closely spaced programmer antenna. The RF telemetry antenna is positioned outside the hermetically sealed IMD housing, which allows it to operate in a high frequency RF telemetry bandwidth and reduces space requirements inside the housing. The RF telemetry antenna is connected to an antenna feedthrough.

A RF telemetry module is connected to the antenna feedthrough and the RF telemetry antenna within the hermetically sealed IMD housing. The RF telemetry module is also connected to an IMD circuit board. Since there is limited space inside the hermetically sealed IMD housing, the RF telemetry module may not be positioned in the same plane as the IMD circuit board. Because of this orientation, the connection between the RF telemetry module and IMD circuit board may not be automated, thereby adding cost and time to the manufacturing of the IMD with RF capability.

Accordingly, it is desirable to provide a connection between a RF module and an IMD circuit board inside an IMD housing that accommodates automated assembly of the two components. Furthermore, other desirable features and characteristics of the present invention will become apparent from the subsequent detailed description and the appended claims, taken in conjunction with the accompanying drawings and the foregoing technical field and background.

BRIEF SUMMARY

A laser ribbon bond pad array connector is disclosed for electrically connecting a RF module to an IMD circuit board in an implantable medical device (IMD). When placing an RF module into the hermetically sealed housing of the IMD, there is very little space. To fit the RF module inside the housing, it is positioned at an angle to the IMD circuit board. The array connector disclosed herein re-positions the bonding pads of the RF module into substantially the same plane or parallel plane as the bonding pads on the IMD circuit board. Bonding pads on the array connector may then be electrically connected to the bonding pads on the RF module by automated means, such as laser ribbon bonding.

An apparatus is provided for an array connector that includes a connector body with a plurality of electrically isolated bonding fingers embedded in the connector body. Each bonding finger includes a solder pad that is exposed on a first surface of the connector body and a laser ribbon bond pad that is exposed on a second surface of the connector body. The first and second surfaces may be perpendicular or approximately perpendicular to each other. The solder pads are configured to electrically couple with bonding pads on an RF module and the laser ribbon bond pads are configured for laser ribbon bonding.

A RF module is disclosed for use in an implantable medical device that includes a body with a plurality of bonding pads and one or more array connectors. The one or more array connectors include a plurality of solder pads electrically coupled to the plurality of bonding pads on the body and a plurality of laser ribbon bond pads configured for laser ribbon bonding with bond pads of an IMD circuit board An implantable medical device is disclosed that includes a housing with an IMD circuit board and a RF module positioned within the housing. The RF module is positioned within the housing at an angle to the IMD circuit board. The IMD circuit board includes a plurality of IMD circuit board bonding pads. The RF module includes a body with a plurality of bonding pads and one or more array connectors. The one or more array connectors include a plurality of solder pads that are electrically coupled to the plurality of bonding pads on the body and a plurality of laser ribbon bond pads. The plurality of laser ribbon bond pads are electrically connected to the plurality of IMD circuit board bonding pads.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

For the sake of brevity, conventional techniques related to signal processing, data transmission, and other functional aspects of the RF systems (and the individual operating components of the RF systems) may not be described in detail herein.

The present invention will be described in relation to a particular IMD design using RF telemetry, but it is not intended that the invention be limited to any particular design when it can be advantageously implemented in various types of IMDs, such as ICDs, pacemaker-cardioverter-defibrillators, drug delivery pumps, cardiomyostimulators, cardiac and other physiologic monitors, nerve and muscle stimulators, deep brain stimulators, cochlear implants, artificial hearts, etc.

Figure 1:
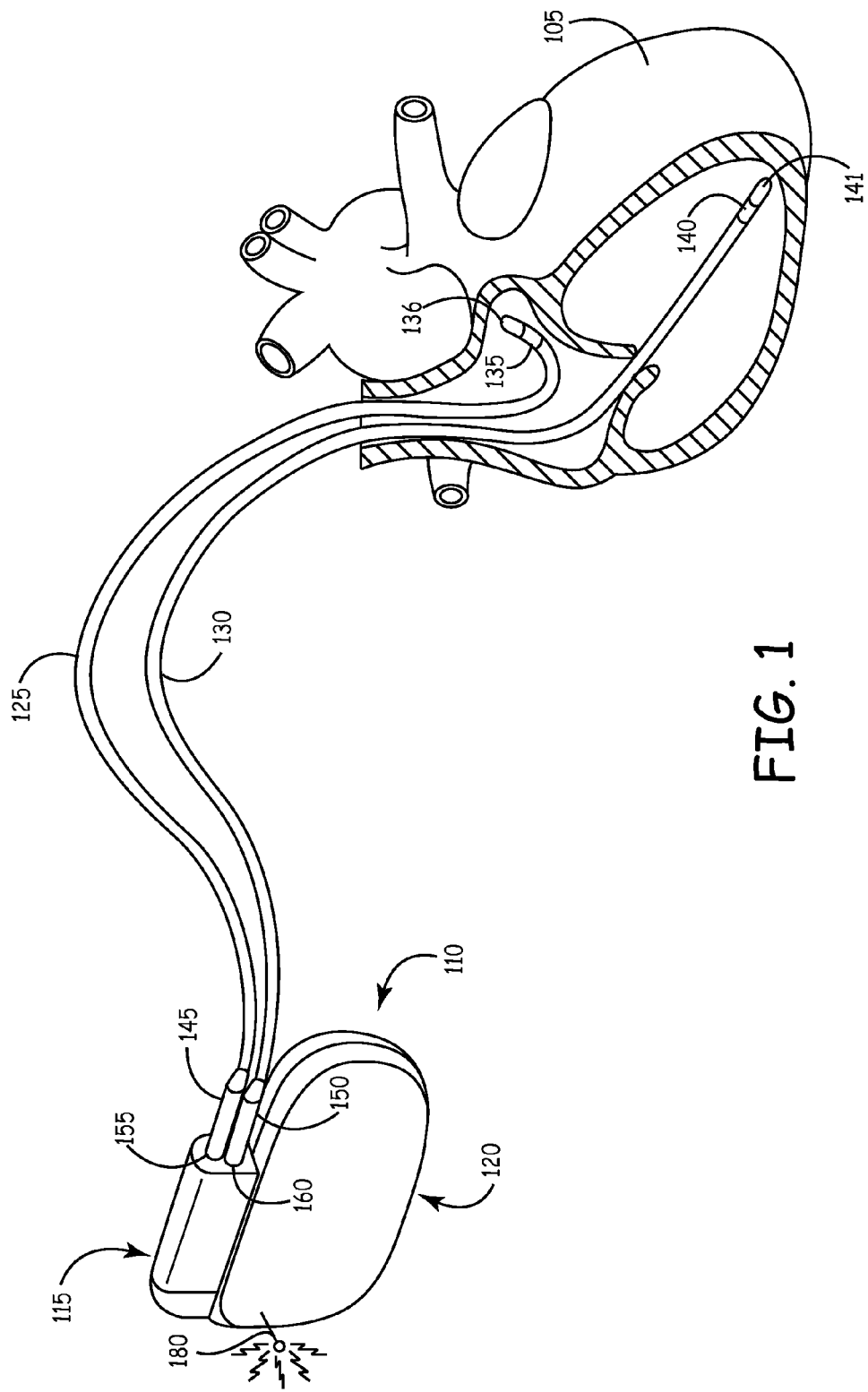
FIG. 1 is a simplified schematic view showing an implantable medical device in relation to a human heart.

FIG. 1 depicts an implantable medical device (IMD) 110, shown as a dual chamber pacemaker IPG, as it relates to patient's heart 105. The IMD 110 includes a connector header 115 and a hermetically sealed enclosure 120. Atrial and ventricular pacing leads 125 and 130 extend from the connector header 115 to the right atrium and ventricle, respectively. Atrial electrodes 135 and 136 disposed at the distal end of the atrial pacing lead 125 are located in the right atrium. Ventricular electrodes 140 and 141 at the distal end of the ventricular pacing lead 130 are located in the right ventricle.

The connector header 115 establishes electrical and mechanical connections of proximal connector end assemblies 145 and 150 of the atrial and ventricular pacing leads 125 and 130 to electrical or electronic circuitry disposed within hermetically sealed enclosure 110. Connector header 115 therefore preferably incorporates connector blocks (not shown) within the connector header housing that are aligned with elongated lead connector end receptacles 155 and 160, and that are adapted to receive lead connector end assemblies 145 and 150. Any other lead, fixation mechanism, and/or electrode configuration known in the art may be used with the current invention, and those shown are exemplary only. Feedthroughs and feedthrough pins connected to the connector blocks and extending through the hermetically sealed enclosure 120 are not shown in FIG. 1. Connector header 115 may be molded of a rigid thermoplastic material such polyurethane, polysulfone or any other such suitable medical grade thermoplastic material.

While atrial and ventricular pacing leads are shown in FIG. 1, other leads are contemplated at other locations in the body that may monitor and/or deliver therapy. For example, other embodiments may include neuro leads for neuro therapy systems; drug leads drug delivery systems; stimulation leads for stimulation therapy systems; sensor leads for monitoring activity; or other compatible monitor and/or treatment delivery leads for other systems.

The IMD 110 also includes an IMD RF telemetry antenna 180 electrically coupled to the telemetry circuitry on an RF module. The IMD RF telemetry antenna 180 may by any compatible RF telemetry antenna, such as a surface mounted antenna. In one embodiment, the IMD RF telemetry antenna 180 is incorporated into the connector header.

Figure 2:
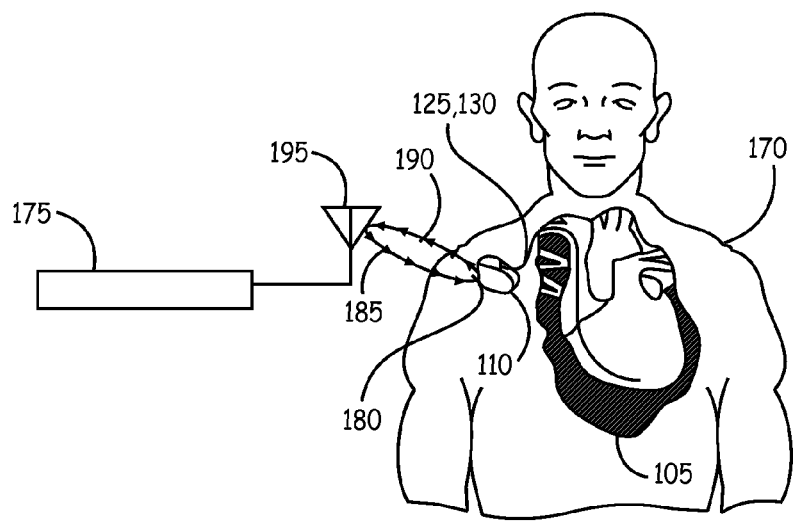
FIG. 2 a simplified schematic view of the implantable medical device communicating with an external device by RF telemetry.

FIG. 2 illustrates RF telemetry communication between the IMD 110 and an external device 175, such as a programmer. While a dual chamber pacemaker IPG is shown, other IMDs would communicate similarly. The IMD 110 is implanted in the patient 170 beneath the patient's skin or muscle. The IMD 110 is electrically coupled to the heart 105 of the patient 170 through pace/sense, cardioversion/defibrillation electrodes or lead conductor(s), such as endocardial leads 125, 130. The endocardial leads 125, 130 are also electrically coupled to the connector header 115. The IMD 110 contains a battery and an operating system powered by the battery that may employ a microcomputer or a digital state machine for timing and controlling device functions in accordance with a programmed operating mode. The operating system includes memory registers in RAM for storing a variety of programmed-in operating mode and parameter values that are used by the operating system. The memory registers may also be used for storing data compiled from sensed cardiac activity and/or relating to device operating history or sensed physiologic parameters for telemetry out on receipt of a retrieval or interrogation instruction.

Information is communicated by RF transmissions between the IMD 110 and the external device 175. In one embodiment, the system uses short range RF downlink telemetry (DT) transmissions 185 and uplink telemetry (UT) transmissions 190. Programming commands or data are transmitted between the IMD RF telemetry antenna 180 and an external RF telemetry antenna 195 associated with the external device 175. In an uplink telemetry transmission 190, the external RF telemetry antenna 195 operates as a telemetry receiver antenna, and the IMD RF telemetry antenna 180 operates as a telemetry transmitter antenna. Conversely, in a downlink telemetry transmission 185, the external RF telemetry antenna 195 operates as a telemetry transmitter antenna, and the IMD RF telemetry antenna 180 operates as a telemetry receiver antenna.

Figure 3:
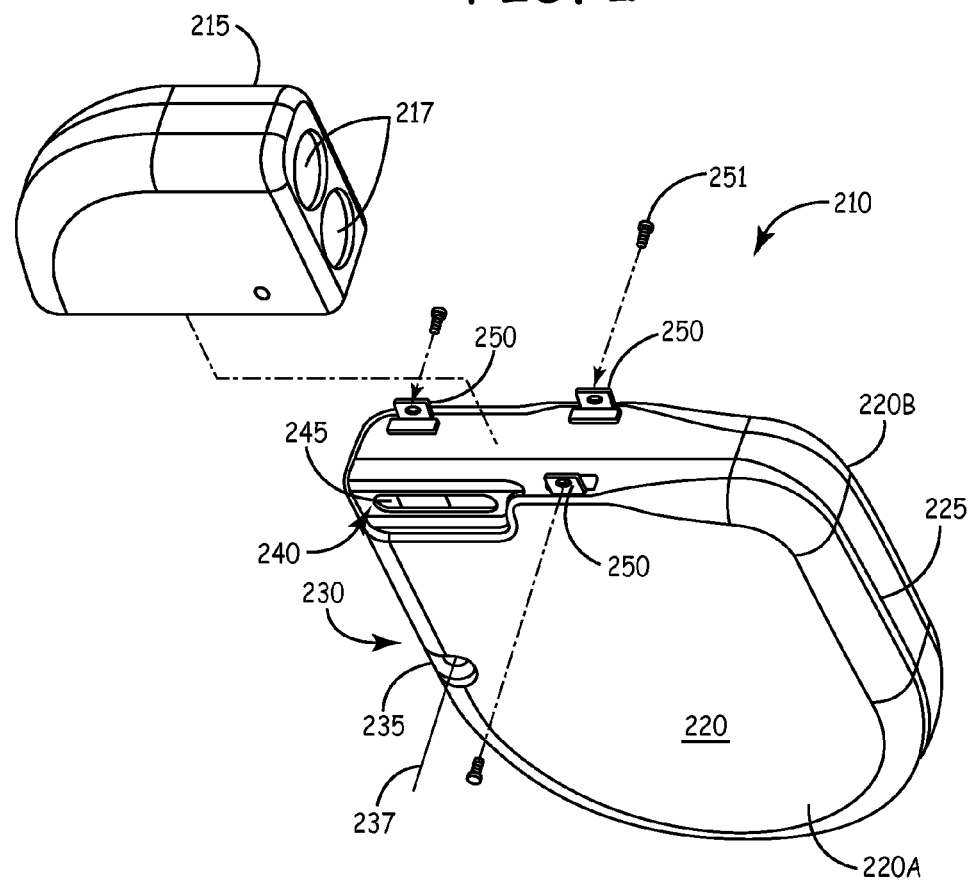
FIG. 3 is a simplified exploded perspective view showing the attachment of a connector header to the housing.

FIG. 3 is a perspective view showing one embodiment of an IMD 210 that includes a connector header 215 and a hermetically sealed housing 220. One or more leads, such as leads 125, 130 described above, are adapted to be coupled to receptacles 217 of the connector header 215 in a manner known in the art. The hermetically sealed housing 220 is typically formed of a thin walled biocompatible material shaped in half sections, first shield 220a and second shield 220b that are welded together in a seam 225. The housing 220 may be made of medical grade material, such as titanium, nickel-cobalt, gold, stainless steel, or any other such suitable medical grade material that is weldable. A telemetry recess 230 is formed in first side 220a that includes a telemetry feedthrough hole that a telemetry antenna feedthrough 235 is welded in. The telemetry antenna feedthrough may by any suitable type, such as a coaxial antenna feedthrough. A connector recess 240 is formed in first side 220a that includes an elongated feedthrough hole that accommodates connector header feedthrough 245. Connector tabs 250 are positioned on the housing 220 for attachment of the connector header 215 with pins 251. An antenna 237, such as IMD RF telemetry antenna 180 shown in FIG. 1, is coupled to antenna feedthrough 235 by known means. In one embodiment, the antenna 237 is a separate antenna. In another embodiment, the antenna 237 is part of the connector header 215.

Figure 4:
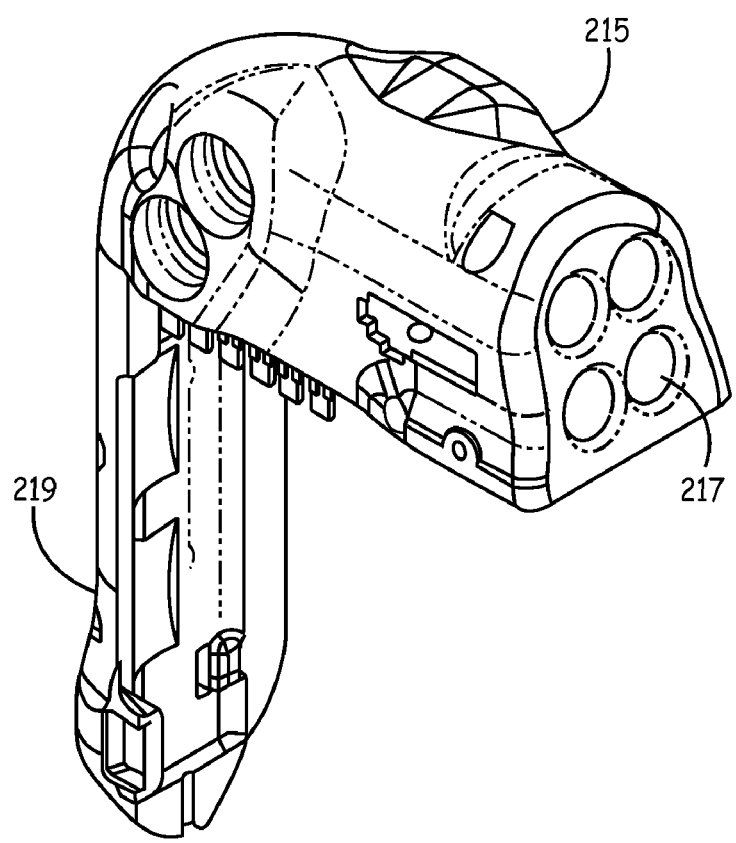
FIG. 4 is a perspective view showing an alternate embodiment of a connector header.

FIG. 4 is a perspective view showing an alternate embodiment of a connector header 215 having an extension portion 219. The extension portion 219 may house or cover an antenna.

Figure 5:
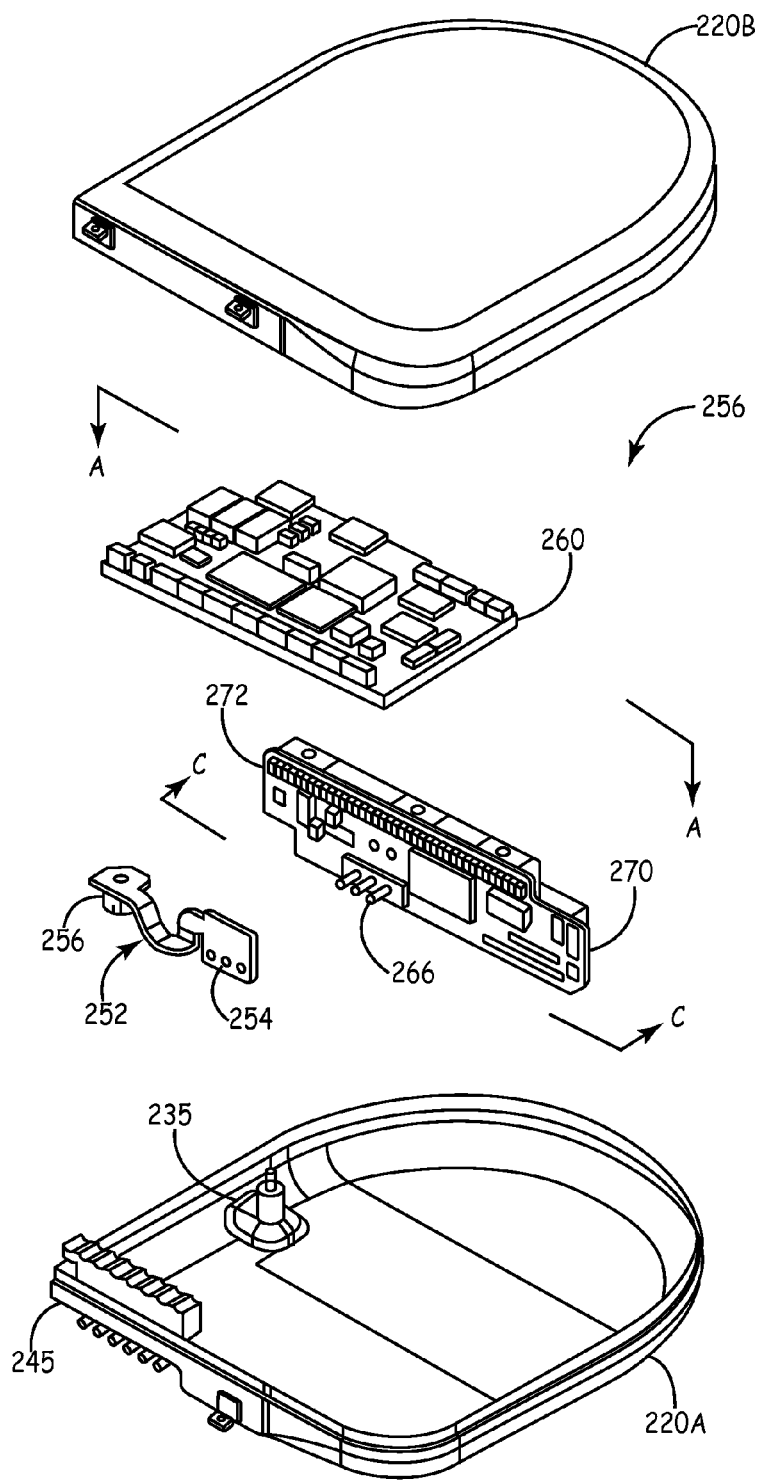
FIG. 5 is a simplified exploded perspective view of the housing showing some of the internal components.

FIG. 5 is an exploded perspective view of the housing 220 shown in FIG. 3. In the embodiment shown, the internal components include an IMD circuit board 260 electrically coupled to a RF module 270 using one or more laser ribbon bond pad array connectors ("array connector") 272. The RF module 270 is also coupled to the antenna feedthrough 235. In the embodiment shown, the RF module 270 is coupled to the antenna feedthrough 235 by a RF antenna interconnect 252. The RF antenna interconnect 252 includes one or more sockets 254 that are designed to electrically couple to one or more pins 266 on the RF module 270 and an antenna socket 256 coupled to the antenna feedthrough 235. One such RF antenna interconnect is disclosed in co-pending patent application titled "RADIO FREQUENCY ANTENNA FLEXIBLE CIRCUIT INTERCONNECT WITH UNIQUE MICRO CONNECTORS", Ser. No. 10/973,137, filed Oct. 26, 2004, which is incorporated by reference. In another embodiment not shown, the RF module 270 may include an antenna socket 256 as part of the RF module 270, the antenna socket 256 being directly coupled to the antenna feedthrough 235 without using an RF antenna interconnect. Many of the components for the IMD are omitted for clarity and are known to those skilled in the art.

Figures 6, 7:
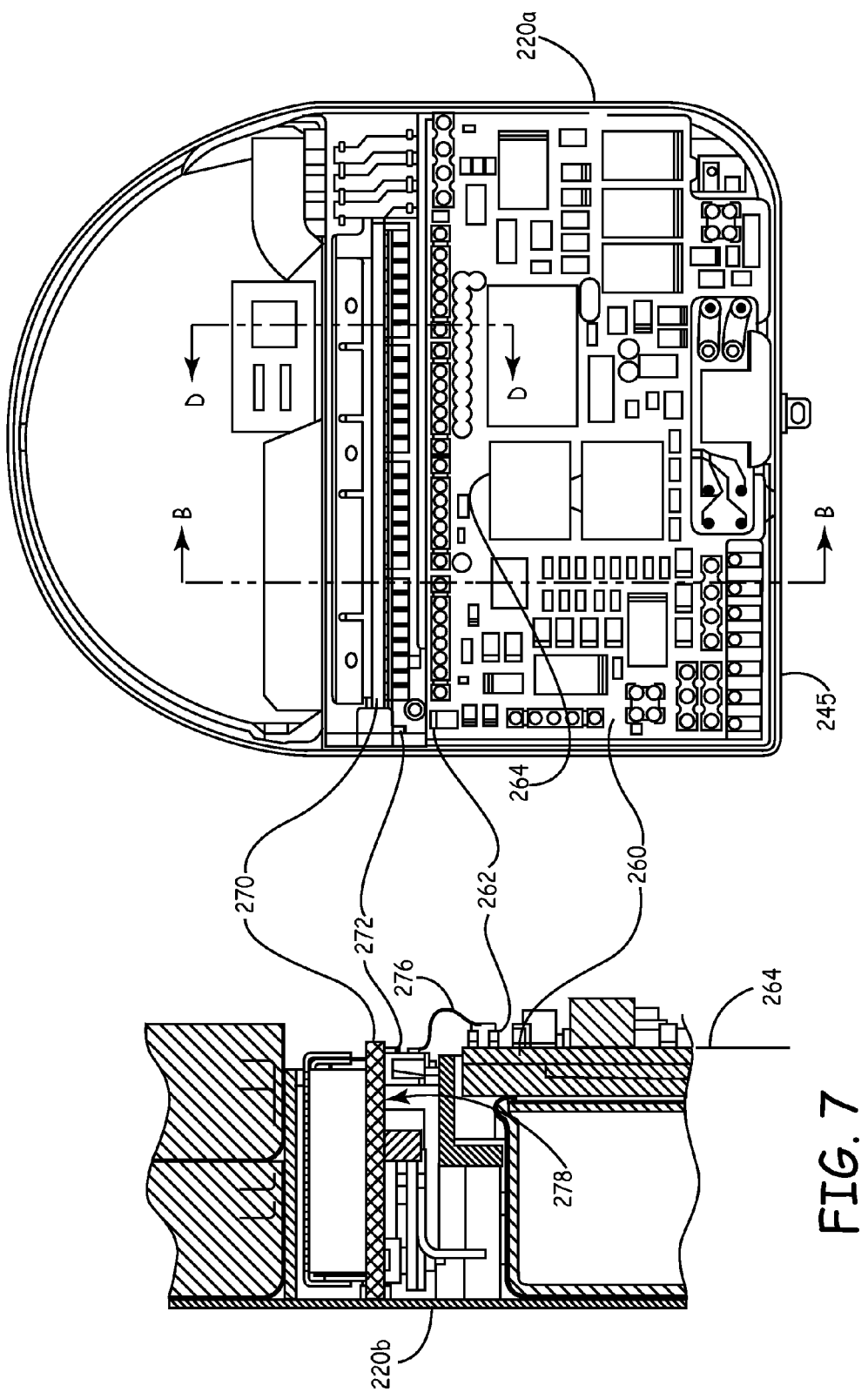
FIG. 6 is a view at A—A of FIG. 5 showing the IMD circuit board and RF module installed into the housing.
FIG. 7 is a cross-sectional view at B—B of FIG. 6.

FIG. 6 is a view at A—A of FIG. 5 showing the IMD circuit board 260 and RF module 270 installed into the housing 220a and FIG. 7 is a cross-sectional view at B—B of FIG. 6. As can be seen in the figures, the IMD circuit board 260 takes up the majority of the space in the housing 220a. Because of this, the RF module 270 is positioned at an angle to the IMD circuit board 260. While the angle shown in the figures between the RF module 270 and the IMD circuit board 260 is 90 degrees, it can be any angle, ranging from approximately 45 to approximately 90 degrees. One drawback to this placement is that bonding pads (not shown) on the surface 278 of the RF module 270 are at 90 degrees to bonding pads 262 on the surface 264 of the IMD circuit board 260. Connecting wiring between bonding pads on non-planer surfaces is time consuming and not compatible with automated processes for wiring parallel or planer surfaces known in the art, such as laser ribbon bonding. To solve this problem, the present invention uses an array connector, such as array connector 272 described herein, to re-position bonding pads of the RF module 270 into substantially the same plane or parallel plane as the bonding pads 262 on the IMD circuit board 260. Bonding pads 288 on the array connector 272 are then electrically connected to the bonding pads 262 on the RF module 270 by electrical connections 276.

Figure 8:
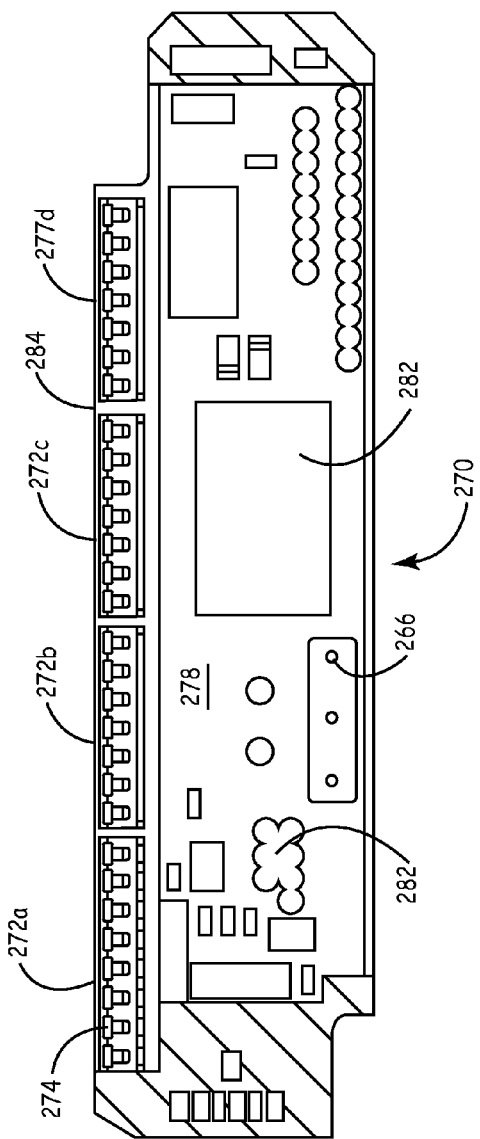
FIG. 8 is a view taken at C—C of FIG. 5 showing the RF module with laser ribbon bond pad array connectors.

FIG. 8 is a view taken at C—C of FIG. 5 showing the RF module 270 and array connectors 272a–272d. While four array connectors are shown on the RF module 270 in the figures, any suitable number may be used. The RF module 270 may be an integrated circuit (IC) board, printed wiring board (PWB), or any other suitable electronic device. One or more electronic components 282 may be attached to the surface 278 of the RF module 270 and interconnected by traces or vias known in the art. Bonding pads (not shown) on the surface 278 of the RF module 270 are positioned proximate an edge 284. The array connectors 272a–272d are positioned over the bonding pads (not shown) and joined to them by known means, such as reflow soldering.

Figure 9:
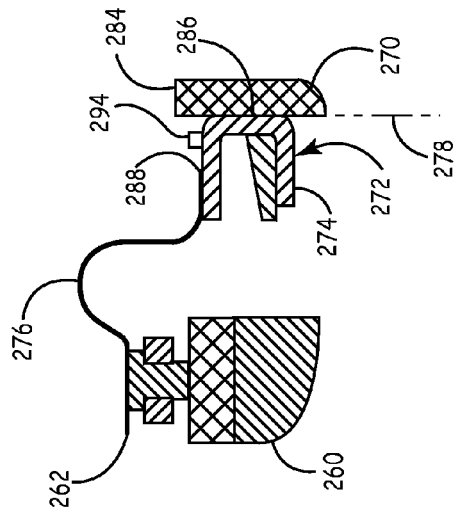
FIG. 9 is a cross-sectional view taken at D—D of FIG. 6 showing a laser ribbon connection between the laser ribbon bond pad array connector mounted on the RF module and the IMD circuit board.

FIG. 9 is a cross-sectional view taken at D—D of FIG. 6 showing the array connector 272 mounted on the RF module 270 proximate the edge 284 and connected to the IMD circuit board 260. The array connector 272 allows for electrical connections 276 between the RF module 270 and IMD circuit board 260 be done in the same or parallel plane. To accomplish this, the array connector 272 has a plurality of bonding fingers 274 that are electrically isolated from each other. Each finger 274 includes an exposed solder pad 286 on a first surface that is linked to an exposed laser ribbon bond pad 288 on a second surface. The exposed solder pads 286 form a solder pad array for attachment to bonding pads on the surface of the RF module 270. The exposed laser ribbon bond pads 288 form a laser ribbon bond pad array for attachment to the IMD circuit board 260. The two arrays are oriented at 90 degrees from each other. The array connector 272 is configured to allow for electrical interconnection between the RF module 270 and the IMD circuit board 260. While a 90 degree angle between the RF module 270 and IMD circuit board 260 is shown, the invention is not limited to 90 degrees. During assembly, the solder pads 286 of the solder pad array are soldered, for example by reflow soldering, to the corresponding bonding pads (not shown) on surface 278 of the RF module 270. When joined, the laser ribbon bond pads 288 are positioned at 90 degrees to the surface 278 of the RF module 270, such that when RF module 270 is in place within the IMD housing, the laser ribbon bond pads 288 of the laser ribbon bond pad array are parallel or planer to the bonding pads 262 on the surface 264 of the IMD circuit board 260. The laser ribbon bond pads 288 of the laser ribbon bond pad array may then be electrically coupled 276 the bonding pads 262 by automated means, such as laser ribbon bonding or wire bonding.

Figure 10:
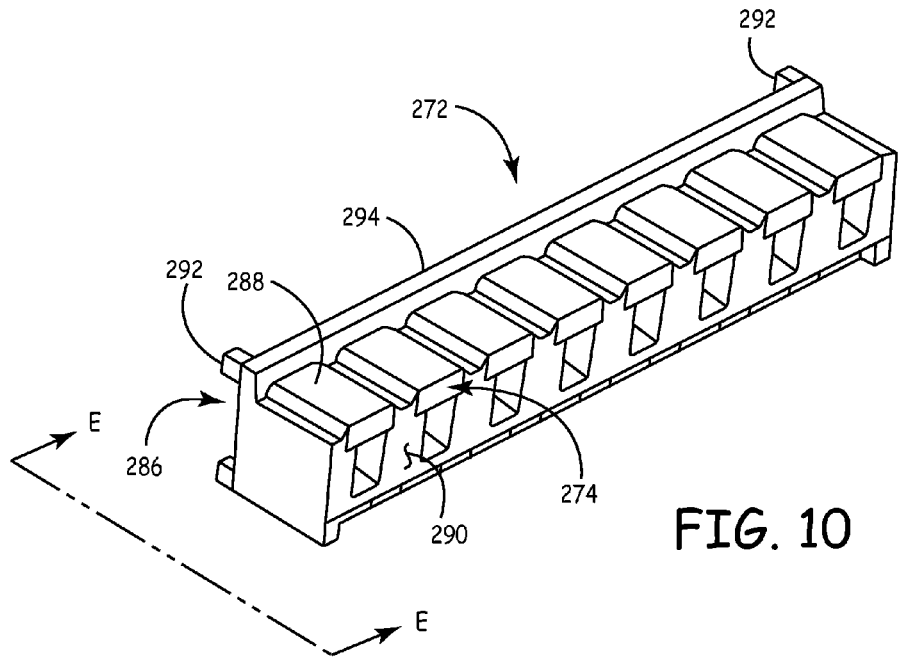
FIG. 10 is a perspective view showing one embodiment of a laser ribbon bond pad array connector.

FIG. 10 is a perspective view showing one embodiment of a laser ribbon bond pad array connector 272 that includes the plurality of bonding fingers 274 separated by the connector body 290 made of electrically insulating material. While the embodiment shown in FIG. 10 has eight bonding fingers, any appropriate number may be used. Each of the bonding fingers 274 include two exposed pads separated by 90 degrees. The first is the solder pad 286 that is configured to be joined by soldering to a bonding pad on the surface 278 of the RF module 270. The second is the laser ribbon bond pad 288 configured to be laser ribbon bonded to bonding pads 262 on the surface 264 of the IMD circuit board 260 (see FIG. 9).

Figure 11:
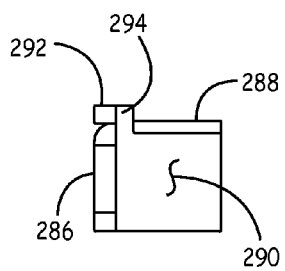
FIG. 11 is an end view taken at E—E of FIG. 10 showing more details of the laser ribbon bond pad array connector.

FIG. 11 is an end view taken at E—E of FIG. 10 showing more details of the array connector 272. A plurality of offsets or feet 292 are positioned on the side of the array connector 272 having the solder pads 286. During installation on the RF module 270, the feet 292 provide a uniform distance from the solder pad 286 to the RF module 270 for consistent reflow soldering. To prevent solder from wicking up to the laser ribbon bond pads 288 during reflow soldering, a solder dam 294 is provided between the solder pad 286 and the laser ribbon bond pad 288. The feet 292 and the solder dam 294 may be separate components or may be part of the connector body 290.

The bonding fingers 272 are overmolded by the insulating material of the connector body 290 by injection molding. The bonding fingers 272 may be pre-stamped to shape using a electrically conductive material capable of withstanding the high heat in the reflow solder process and the laser ribbon bonding process. One suitable material is nickel, such as Ni 200. The bonding fingers 272 may also be gold plated. The connector body 290 is made of an electrically insulating material. The connector body 290 may be made from a high temperature thermoplastic material, such as an amorphous thermoplastic polyetherimide (Ultem®), that is compatible with injection molding, and also capable of withstanding the high heat in the solder process and laser ribbon bonding process.

Figure 12:
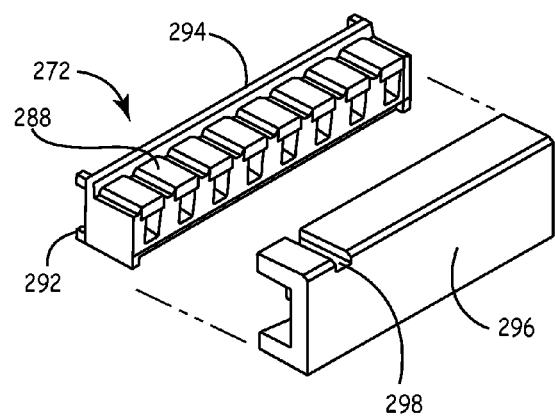
FIG. 12 shows an assembly cover that may be used with the laser ribbon bond pad array connector.

FIG. 12 shows an assembly cover 296 that may be used with the array connector 272 to aid in assembly to the RF module 270. The assembly cover 296 may be made of a plastic material. In use, the assembly cover 296 is removably attached to the array connector 272 while allowing exposure of the solder pads 286 of the solder pad array. The assembly cover 296 performs a number of functions. First, the assembly cover 296 may be configured to aid automated RF module assembly for placement of the array connector 272. For example, in one embodiment the assembly cover 296 may be compatible with a "pick & place" machine that picks up the array connector 272, transports it to the correct location and then places it on the RF module for reflow soldering. First, to aid in positioning, the assembly cover 296 may have one or more notches 298 or marks compatible with a placement system or vision system that uses the notches 298 for precise placement. Second, the assembly cover 296 may be used to protect the array connector during storage and transit. Third, the assembly cover 296 may work in conjunction with the solder dam 294 to protect the exposed laser ribbon bond pads 288 of the laser ribbon bond pad array from solder during the reflow soldering operation.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. An array connector for use in electrically connecting a first electrical component to a second electrical component in an implantable medical device, comprising:
    a connector body having a first surface and a second surface;
    a plurality of electrically isolated bonding fingers embedded in the connector body, each bonding finger having:
        a solder pad on the first surface; and
        a laser ribbon bond pad on the second surface.

2. The array connector of claim 1, wherein the solder pads of the plurality of bonding fingers form a solder pad array configured to couple with bonding pads on the first electrical component.

3. The array connector of claim 1, wherein the laser ribbon bond pads of the plurality of bonding fingers form a laser bond pad array configured for laser ribbon bonding with bond pads of the second electrical component.

4. The array connector of claim 1, wherein the first surface is substantially perpendicular to the second surface.

5. The array connector of claim 1, wherein the connector body is formed from an electrically insulating material.

6. The array connector of claim 1, wherein the connector body is formed from a high temperature thermoplastic.

7. The array connector of claim 1, wherein the connector body is formed from an amorphous thermoplastic polyetherimide.

8. The array connector of claim 1, wherein the bonding fingers are pre-stamped metal contacts.

9. The array connector of claim 1, wherein the bonding fingers are made of electrically conductive material.

10. The array connector of claim 1, wherein the bonding fingers are made of nickel.

11. The array connector of claim 10, wherein the bonding fingers are gold plated.

12. The array connector of claim 1, further comprising a plurality of feet positioned on the first surface of the connector body.

13. The array connector of claim 12, wherein the plurality of feet part of the connector body.

14. The array connector of claim 1, further comprising a solder dam positioned between the solder pads and the laser ribbon bond pads.

15. The array connector of claim 14, wherein the solder dam is part of the connector body.

16. The array connector of claim 1, further comprising an assembly cover configured to cover at least the laser ribbon bond pads.

17. The array connector of claim 16, wherein the assembly cover further includes a notch configured to work with a placement system.

18. An electronic component for use in an implantable medical device, comprising:
    a body;
    a plurality of bonding pads positioned on the body;
    one or more array connectors having:
        a connector body having a first surface and a second surface; and
        a plurality of bonding fingers, the bonding fingers having a plurality of solder pads on the first surface being electrically coupled to the plurality of bonding pads on the body and a plurality of laser ribbon bond pads on the second surface.

19. The electronic component of claim 18, further comprising one or more electronic components positioned on the body; the bonding pads being electrically connected to the one or more electronic components.

20. The electronic component of claim 18, further comprising an antenna socket configured to couple with an antenna feedthrough.

21. The electronic component of claim 18, wherein the body is a printed wiring board.

22. The electronic component of claim 18, wherein the first surface is substantially perpendicular to the second surface.

23. The electronic component of claim 18, wherein the plurality of bonding pads are electrically coupled to the plurality of solder pads by reflow soldering.

24. An array connector for use in an implantable medical device, comprising:
   an insulative connector body; and
   an array of electrically isolated bonding fingers disposed on the insulative connector body, each bonding finger in the array having a substantially L-shaped profile and comprising:
   a laser ribbon bonding pad; and
   a solder pad electrically coupled to the laser ribbon bonding pad and forming an angle therewith of approximately 90 degrees.

* * * * *

UNITED STATES PATENT AND TRADEMARK OFFICE
CERTIFICATE OF CORRECTION

PATENT NO. : 7,214,068 B2 Page 1 of 1
APPLICATION NO. : 11/004175
DATED : May 8, 2007
INVENTOR(S) : Kronich et al.

It is certified that error appears in the above-identified patent and that said Letters Patent is hereby corrected as shown below:

In column 8, line 31 please change "of feet part" to --of feet is part--.

Signed and Sealed this

Eighteenth Day of September, 2007

JON W. DUDAS
*Director of the United States Patent and Trademark Office*